United States Patent

Durlacher et al.

[11] Patent Number: 5,562,664
[45] Date of Patent: Oct. 8, 1996

[54] DRILL GUIDE WITH TARGET PCL-ORIENTED MARKING HOOK

[75] Inventors: Scott M. Durlacher; Richard D. Grafton; Reinhold Schmieding, all of Naples, Fla.; Craig D. Morgan, Greenville, Del.

[73] Assignee: Arthrex Inc., Naples, Fla.

[21] Appl. No.: 389,240

[22] Filed: Feb. 15, 1995

Related U.S. Application Data

[63] Continuation-in-part of Ser. No. 122,308, Sep. 17, 1993, Pat. No. 5,409,494, which is a continuation of Ser. No. 837,886, Feb. 20, 1992, Pat. No. 5,269,786.

[51] Int. Cl.$^6$ .................................................. A61F 5/04
[52] U.S. Cl. .................................. 606/96; 606/88; 606/103
[58] Field of Search .................................. 606/96, 97, 98, 606/99, 100, 101, 102, 103, 86, 88, 205, 211; 623/13

[56] References Cited

U.S. PATENT DOCUMENTS

| | | | |
|---|---|---|---|
| 4,672,957 | 6/1987 | Hourahane | 606/80 |
| 4,739,751 | 4/1988 | Sapega | 606/96 |
| 4,781,182 | 11/1988 | Purnell | 606/96 |
| 4,813,407 | 3/1989 | Vogen | 606/86 |
| 4,823,780 | 4/1989 | Odensten | 606/96 |
| 4,883,048 | 11/1989 | Purnell | 606/96 |
| 4,920,958 | 5/1990 | Walt | 606/96 |
| 4,945,904 | 8/1990 | Bolton | 606/96 |
| 4,952,213 | 8/1990 | Bowman | 606/88 |
| 5,009,661 | 4/1991 | Michelson | 606/170 |
| 5,037,426 | 8/1991 | Goble et al. | 606/96 |
| 5,112,335 | 5/1992 | Laboureau | 606/88 |
| 5,112,337 | 5/1992 | Paulos | 606/96 |
| 5,139,520 | 8/1992 | Rosenberg | 623/13 |
| 5,154,720 | 10/1992 | Trott | 606/96 |
| 5,163,940 | 11/1992 | Bourque | 606/88 |
| 5,269,786 | 12/1993 | Morgan | 606/96 |
| 5,350,383 | 9/1994 | Schmieding | 606/96 |
| 5,409,494 | 4/1995 | Morgan | 606/96 |

FOREIGN PATENT DOCUMENTS

| | | | |
|---|---|---|---|
| 350780 | 1/1990 | European Pat. Off. | 606/96 |
| 9200773 | 1/1992 | WIPO | 606/96 |

*Primary Examiner*—Robert A. Hafer
*Assistant Examiner*—David J. Kenealy
*Attorney, Agent, or Firm*—Ostrolenk, Faber, Gerb & Soffen, LLP

[57] ABSTRACT

A drill guide for marking a proper location of a bone tunnel for arthroseopic surgery, provided with a marking hook designed to reference the posterior cruciate ligament. The marking hook includes a slot to allow the surgeon to view endoscopically the position of a guide pin as it is drilled through the tibia.

12 Claims, 2 Drawing Sheets

DRILL GUIDE WITH TARGET PCL-ORIENTED MARKING HOOK

This is a continuation-in-part of application Ser. No 08/122 308, filed Sep. 17, 1993, now U.S. Pat. No. 5,409, 494 which is a continuation of application Ser. No. 07/837, 886, filed Feb. 20, 1992, now U.S. Pat. No. 5,269,786, both of which are incorporated herein by reference.

BACKGROUND OF THE INVENTION

1. Field of the Invention

The present invention relates to a drill guide for accurate tibial tunnel placement both inside and outside the knee in endoscopic ACL reconstruction and, more specifically, to a drill guide with a marking hook which references the posterior cruciate ligament and has a slot at its distal end for facilitating drilling of a guide pin.

2. Description of the Related Art

In the past, the intra-articular entry point of the tibial tunnel has tended to be placed too far anterior, resulting in roof impingement and delayed graft failure. See, e.g., S. Howell, "*A Rationale for Predicting ACL Graft Impingement by the Intercondylar Roof, A Magnetic Resonance Imaging Study*", Am. Jour. Sports Med., Vol. 19, No. 3, pp. 276 (1991), incorporated herein by reference. This problem has occurred largely due to the absence of any constant, bony landmarks in the intercondylar notch which can be used to orient placement of guide systems for accurate, reproducible, tibial tunnel guide-pin placement.

Also, the tibial tunnel exit point outside the knee has tended to be placed too close to the joint line. This results in a short tibial tunnel such that the tibial bone plug of a completed bone-patellar-tendon-bone autograft reconstruction resides outside the tibial tunnel and interference screw fixation cannot be used. A second problem caused by a high, tibial-tunnel exit point is that the angle of the tibial tunnel with respect to the joint line is too small, which will not allow transtibial tunnel instrumentation to reach the isometric area on the lateral femoral condyle to create a femoral socket for graft fixation.

The one constant anatomic structure in the intercondylar notch of the anterior cruciate ligament (ACL) deficient knee is the posterior cruciate ligament (PCL). See, e.g., C. Morgan et al., "*Arthroscopic Meniscus Repair Evaluated by Second Look Arthroscopy,*" Am. Jour. Sports Med., Vol. 19, No. 6, p. 62 (1991), herein incorporated by reference. In the intact knee, there is an important anatomic interaction between the ACL and the PCL at their midpoints, whereby the intact ACL actually wraps around or bends over the PCL in terminal extension. This dynamic interaction is an integral part of the "screw home" mechanism of the knee. Ideally, during ACL reconstruction, the entry point in the knee for the tibial tunnel should be made far enough posterior to reconstruct this important relationship between the ACL graft and the intact PCL.

The proper entry point for tibial tunnel guide pin placement resides 7 mm anterior to the leading edge of the PCL at the level of the intercondylar floor. A 7 mm diameter graft placed through a 7 mm tibial tunnel centered at this point will: 1) reach an isometric femoral socket directly in line with the tibial tunnel with the knee in 70–80° of flexion; 2) avoid roof impingement in full extension with a minimal notchplasty; and, 3) reconstruct the "screw home" mechanism and the interaction between the ACL graft and the intact PCL.

Previous instruments have been developed for marking the correct location of the tibial tunnel. See, for example, U.S. Pat. No. 5,269,786. Such instruments use marking hooks which have a tip that disadvantageously blocks a surgeon's view through the arthroscope of the drilling site at the end of the tibial tunnel. Without visual verification, it can be difficult for the surgeon to determine when drilling is complete. Due to the lack of a visual cue for completion of the tunnel drilling, surgeons have often relied upon the impact of the drill upon the marking hook as an indication of completion. However, this is undesirable, since such impact can create metal shavings which may harm the joint and are otherwise undesirable. The impact can also cause deflection of the drill, resulting in peripheral tissue damage or inaccurate tunnel formation.

SUMMARY OF THE INVENTION

The present invention overcomes the above-described deficiencies of the prior art by providing a marking hook. A slot at the distal end of the marking hook allows the surgeon to endoscopically view the drill as it passes through the intercondylar floor. Advantageously, the drill can pass through the slot without impacting the marking hook. The distal end of the marking hook includes an extension for referencing the anatomic structure of the knee, consistently locating the ideal location of the tibial tunnel.

More specifically, the marking hook of the present invention references the base portion of the PCL near its intercondylar floor from an anteromedial portal, and, when used with an appropriate outrigger (described below) accurately and consistently positions a sighting device, so that a guide pin can be delivered to an intra-articular entry point 7 mm from the leading edge of the PCL at the intercondylar floor. The marking hook has a slot near the reference point. The center of the slot intersects the longitudinal axis of the sighting device.

The marking hook and sighting device are positioned relative to each other on an arc-shaped outrigger. The outrigger includes a channel along its length in which an adapter for holding the marking hook is mounted and slidably mounted on the outrigger. Optionally, the sighting device is also mounted to be adjustably slidable. The sighting device receives a guide pin which marks the proper entry point into the knee for drilling of the tibial tunnel, as described in U.S. Pat. No. 5,350,383, the disclosure of which is incorporated herein by reference.

The present invention may be provided in the form of a pair of interchangeable PCL-oriented marking hooks for the left and right knees, respectively, each of which can be used with the drill guide for ACL reconstruction. The interchangeable hooks each include a longitudinal tip which serves as an anchor.

The distal end of each marking hook preferably includes an extension with a crescent-shaped indent adapted to rest against the PCL. Each marking hook includes a slot at its distal end for receiving the tip of a guide pin. The center of the slot is preferably located 7 mm from the central, reference point of the indent where it contacts the PCL.

The method of the present invention includes the steps of attaching the appropriate marking hook to the outrigger with an adapter, sliding the adapter along the channel of the outrigger to a predetermined position corresponding to the angle of the desired tibial tunnel, locking the position of the adapter on the outrigger at that position, inserting the marking hook into the knee of a patient, advancing the sighting device towards the knee until it is directly adjacent the knee, inserting a guide pin into the sighting device, drilling the guide pin into the knee, and removing the marking hook, thereby leaving the guide pin in position for drilling the tibial tunnel.

Other features and advantages of the present invention will become apparent from the following description, when read in conjunction with the accompanying drawings.

DETAILED DESCRIPTION OF THE PREFERRED EMBODIMENT

Figure 1:
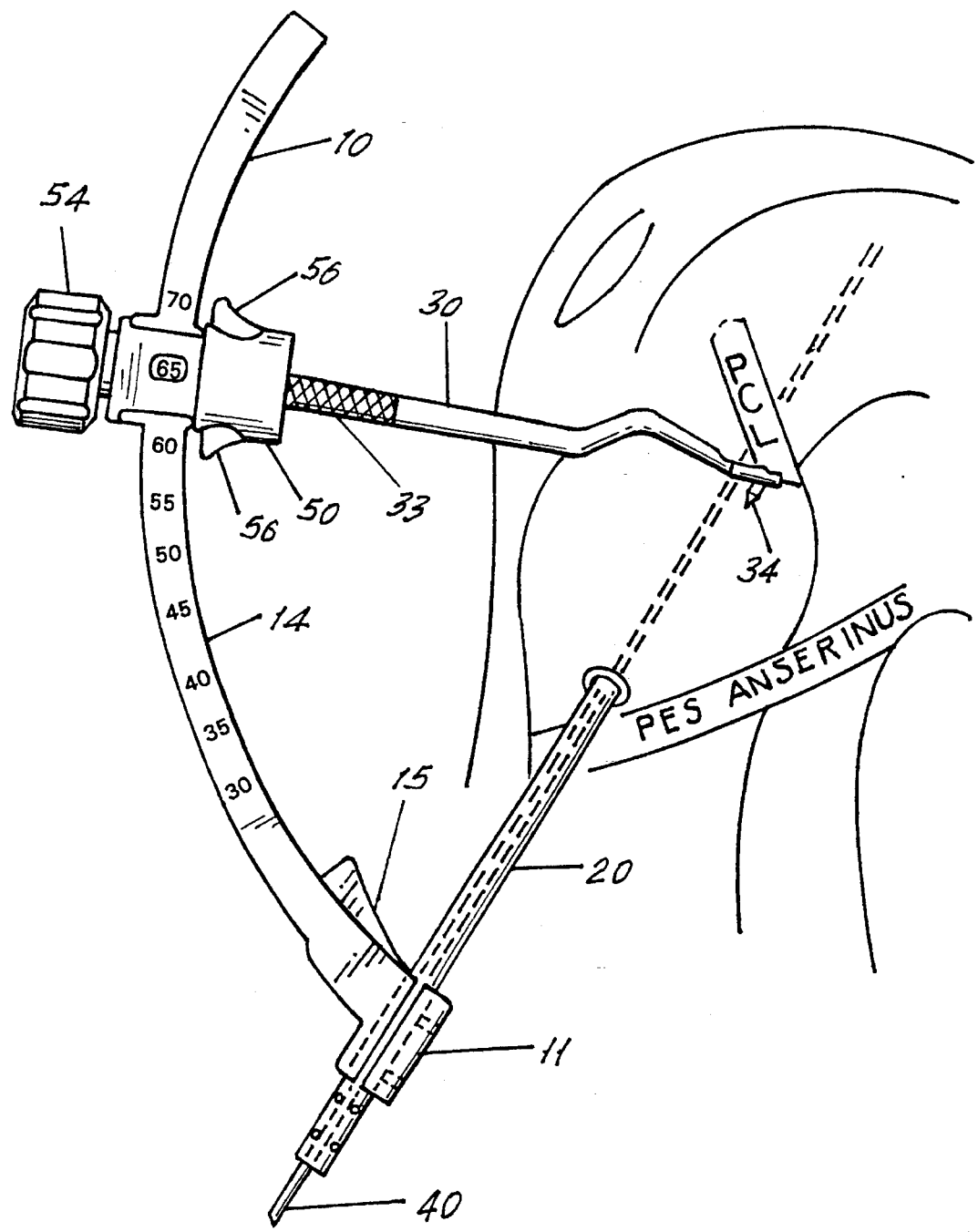
FIG. 1 shows the drill guide of the present invention with the PCL-oriented marking hook in place for locating the tibial tunnel.

Referring to FIG. 1, a tibial drill guide is shown which consists of an outrigger 10, an adjustable sighting device 20, and an interchangeable marking hook 30. The outrigger 10 is arc-shaped, and includes a channel 14 along its length. The channel 14 slidably receives an adapter 50 holding marking hook 30.

Sighting device 20, disposed at one end of the arc of outrigger 10, receives a guide pin 40 which marks the proper location for the tibial tunnel. Sighting device 20 is arranged to be advanced towards the knee into engagement with the skin after it has been properly positioned. With the PCL-reference marking hooks of the present invention, sighting device 20 locates the guide pin 7 mm anterior to the leading edge of the PCL at the intercondylar floor.

As shown in FIG. 1, sighting device 20 is slidably received through a bore 11 located at the lower end of outrigger 10. A spring-loaded trigger release is located adjacent bore 11. When trigger 15 is compressed, sighting device 20 is free to slide within bore 11.

Outrigger 10 extends through a hole in adapter 50. The hole in adapter 50 also receives a screw-nut member 54. When screw-nut member 54 is loosened, adapter 50 is free to slide along channel 14 of outrigger Adapter 50 receives the selected marking hook on the opposite side from screw-nut number 54; i.e., the marking hook is received on the inside of the arc of outrigger 10.

Adapter 50 includes two spring-loaded, pivotable triggers 56 having respective jaws at their inner surfaces (not shown). Each of the marking hooks of the present invention, shown in FIGS. 2-7, includes a collar 32. The collared end of the chosen hook is inserted into the adapter, such that the jaws engage the collar 32 of the hook. When triggers 56 are squeezed, the jaws retract from collar 32, allowing the marking hook to be inserted or removed. Each of the hooks preferably includes a knurled area 33 for grasping the hook.

Figure 2:
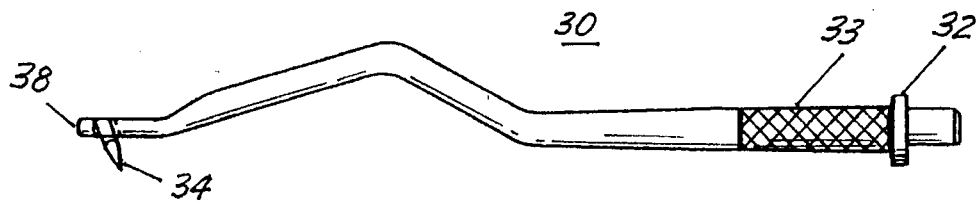
FIG. 2 is a side view of the left tibial marking hook of the present invention.
Figure 3:
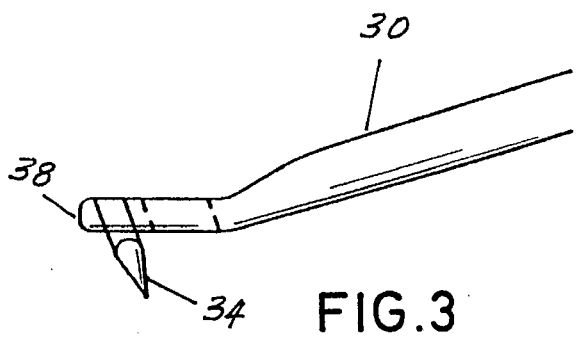
FIG. 3 is a detail side view of the tip of the left tibial marking hook of the present invention.
Figure 4:
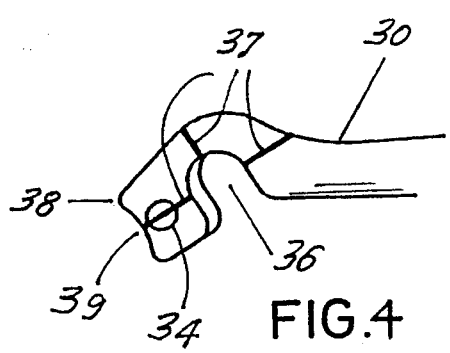
FIG. 4 is a detail top view of the tip of the left tibial marking hook of the present invention.
Figure 5:
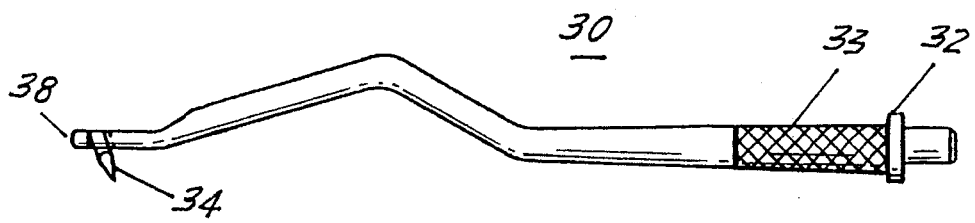
FIG. 5 is a side view of the right tibial marking hook of the present invention.
Figure 6:
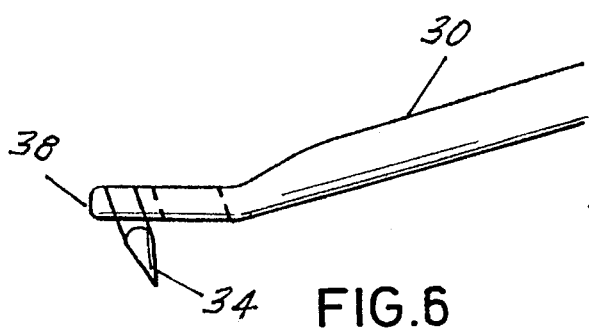
FIG. 6 is a detail side view of the tip of the right tibial marking hook of the present invention.
Figure 7:
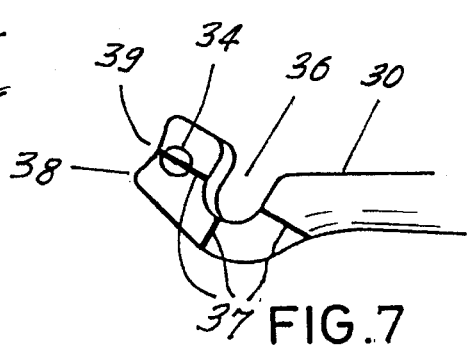
FIG. 7 is a detail top view of the tip of the right tibial marking hook of the present invention.

Two preferred PCL-oriented marking hooks in accordance with the present invention are illustrated in FIGS. 2-7. FIGS. 2-4 illustrate a PCL-oriented, tibial marking hook for the left knee. FIGS. 5-7 illustrate a PCL-oriented, tibial marking hook for the right knee. The left and right hooks shown in FIGS. 2-7 each include a pointed tip 34 for anchoring the hook into bone inside the knee. Tip 34 is preferably angled at about 70° with respect to the longitudinal axis of the hook.

The marking hook of the present invention is provided with a slot 36 located proximal to the tip 34 at the distal end of the hook. Slot 36 allows a surgeon to view the guide pin as it passes through the knee structures on completion of the guide pin drilling operation. Slot 36 also allows the guide pin to pass beyond the marking hook without impinging on the marking hook. As mentioned previously, such contact is undesirable because harmful metal shavings may result, or the contact may raise concerns by the surgeon that deflection of the guide pin has taken place.

Slot 36 advantageously allows the marking hook to be removed from around the guide pin after the guide pin is inserted in place in the knee. The sides and central axis of the opening in slot 36 are preferably angled 60°–70° with respect to the longitudinal axis of the hook, most preferably 65°, to accommodate the guide pin during removal of the hook with adequate clearance. Since the guide pin remains in place during removal of the hook, there is no chance of losing proper pin position or alignment. The open slot design of the hook also requires less metal than a hook with a closed, circular hole.

The center of slot 36 preferably is indicated by target markings 37 to give the surgeon further reference as to where the drill will be coming through the tibial plateau. Preferably, markings 37 are laser-etched onto the surface of the marking hook around the slot. The center of slot 36 indicated by target markings 37 is aligned with sighting device 20.

The marking hooks of the present invention include an extension 38 at the distal end for referencing the PCL. When the hook is inserted into the knee, extension 38 abuts against the base of the PCL. Preferably, the extension 38 has a crescent-shaped indent 39, as shown by the top views in FIGS. 4 and 7, which conforms to the shape of the PCL and allows extension to rest against and cradle the leading edge of the PCL, helping to maintain proper orientation of the marking hook. The center of slot 36 is preferably located 7.0 mm from the middle of the concave surface of indent 39, as measured along the midline of the instrument.

The method of the invention will now be described in conjunction with FIGS. 1-7. First, the appropriate left or right marking hook 30 is chosen and inserted into adapter 50 of outrigger 10. Adapter 50 is then slid along the outrigger (via channel 14) to the appropriate position corresponding to the tunnel angle chosen by the surgeon. Adapter 50 is then locked in position on outrigger 10 by tightening screw member and the marking hook is inserted into the patient's knee through a previously established portal. (This step of the procedure can be reversed; i.e., the marking hook can be inserted into the knee before adjustment and locking on the outrigger).

Next, the hook, mounted on the drill guide, is maneuvered into position by resting it against the PCL and anchored by driving the tip 34 into the tibial plateau. The guide pin is inserted through the sighting device 20 and is attached to a drill. The surgeon starts drilling the guide pin into the knee and continues to do so until he or she sees, endoscopically, that the guide pin has advanced through the slot of the hook. Once drilling of the guide pin is completed, the hook is released from the outrigger. As mentioned previously, the open slot enables the hook to be removed without moving the guide pin. Although previous designs enabled the marking hook to be removed without moving the guide pin, they lacked the advantages of using a slotted hook.

Once the marking hook is removed, the guide pin 40 is left in position so that, for example, a cannulated drill may be placed over the guide pin 40 for drilling the tibial tunnel.

In summary, the drill guide of the present invention with a slotted marking hook provides a device for arthroscopic surgery which, for the first time, allows the surgeon to view the guide pin as it is advanced to the proper depth in the knee. Moreover, the PCL extension provided on the slotted marking hook advantageously allows the surgeon to reference the only constant structure in the knee, i.e. the PCL, to position the guide pin such that the intra-articular guide pin entry point will always be 7 mm anterior to the leading edge of the PCL. The resultant tibial tunnel is also properly angled for drilling a femoral tunnel directly in line with the tibial tunnel.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A drill guide for arthroscopic surgery, comprising:
   an arc shaped outrigger;
   a sighting device coupled to the outrigger, the sighting device having a longitudinal axis and being adapted to receive a guide pin for marking a position for drilling a tibial tunnel; and
   a marking hook attached to the outrigger, the marking hook having a distal end, a proximal end, and a slot located at the distal end and comprising an aperture extending through the marking hook, the aperture having a central axis coinciding with the longitudinal axis of the sighting device.

2. The drill guide of claim 1, wherein the distal end of the marking hook has an extension for contacting an anatomical structure in a patient's knee.

3. The drill guide of claim 2, wherein the anatomical structure is a posterior cruciate ligament, and the extension has a crescent-shaped indent at its distal end for receiving a leading edge of the posterior cruciate ligament.

4. The drill guide of claim 2, wherein the center of the slot is located at a predetermined distance from the distal end of the extension.

5. The apparatus of claim 4, wherein the predetermined distance is 7 mm.

6. The drill guide of claim 1, wherein the slot has an open, semicircular shape to allow removal of the marking hook from around a guide pin passing through the slot.

7. The drill guide of claim 1, wherein the marking hook includes an angled tip proximal to the distal end for anchoring the hook into bone.

8. The drill guide of claim 1, wherein the distal end of the marking hook includes markings around the slot for indicating the location of the center of the slot.

9. The drill guide of claim 1, wherein the outrigger has a longitudinal arcuate channel and an adapter is slidably secured in the channel for attaching the marking hook to the outrigger.

10. The drill guide of claim 9, wherein the adapter is secured in the channel of the outrigger by a screw and nut arrangement.

11. An apparatus for accurately marking a location for a tibial tunnel for arthroscopic anterior cruciate ligament reconstruction by referencing a base of a posterior cruciate ligament at an intercondylar floor, the apparatus comprising:
    a marking hook for referencing a base portion of the posterior cruciate ligament near the intercondylar floor, the marking hook having a distal end and a proximal end, the distal end having a slot for receiving a guide pin, the slot comprising an aperture extending through the marking hook; and
    a sighting device for positioning the guide pin to mark the tibial tunnel location, the sighting device having a longitudinal axis and being coupled to the marking hook by an outrigger such that the guide pin is positioned to locate the tibial tunnel at a predetermined distance from the base of the posterior cruciate ligament at the intercondylar floor, the aperture of the marking hook having a central axis coinciding with the longitudinal axis of the sighting device.

12. A method of marking a proper location of a tibial tunnel for arthroscopic anterior cruciate ligament reconstruction using a drill guide, the drill guide comprising an arc shaped outrigger, a sighting device coupled to the outrigger, the sighting device having a longitudinal axis and being adapted to receive a guide pin for marking the tibial tunnel position, and a marking hook having a distal end, a proximal end and a slot located at the distal end and comprising an aperture extending through the marking hook, the aperture having a central axis coinciding with the longitudinal axis of the sighting device, the method comprising the steps of:
    mounting the proximal end of the marking hook onto the outrigger, the marking hook having a tip located at the distal end for anchoring the hook in tissue, and an extension disposed at the distal end for abutting against the base of a posterior cruciate ligament and positioning the slot at a predetermined distance from a leading edge of the posterior cruciate ligament at the intercondylar floor;
    inserting the distal end of the marking hook into a knee requiring anterior cruciate ligament reconstruction;
    advancing the sighting device towards the knee until it is directly adjacent the knee;
    inserting a guide pin into the sighting device, the guide pin being automatically aligned with the center of the slot;
    drilling the guide pin into the knee; and
    removing the marking hook, thereby leaving the guide pin in position for drilling a tibial tunnel.

* * * * *